(12) United States Patent
Olgun

(10) Patent No.: US 10,085,711 B2
(45) Date of Patent: Oct. 2, 2018

(54) STETHOSCOPE PROTECTIVE COVER

(71) Applicant: Aydin Olgun, Huntington, NY (US)

(72) Inventor: Aydin Olgun, Huntington, NY (US)

(*) Notice: Subject to any disclaimer, the term of this patent is extended or adjusted under 35 U.S.C. 154(b) by 0 days.

(21) Appl. No.: 15/284,010

(22) Filed: Oct. 3, 2016

(65) Prior Publication Data

US 2017/0095224 A1    Apr. 6, 2017

Related U.S. Application Data

(60) Provisional application No. 62/236,380, filed on Oct. 2, 2015.

(51) Int. Cl.
*A61B 7/02* (2006.01)
*A61B 46/10* (2016.01)
*A61B 50/20* (2016.01)

(52) U.S. Cl.
CPC .............. *A61B 7/02* (2013.01); *A61B 46/10* (2016.02); *A61B 50/20* (2016.02)

(58) Field of Classification Search
CPC ............ A61B 46/10; A61B 7/02; A61B 50/20
USPC .......................................................... 181/131
See application file for complete search history.

(56) References Cited

U.S. PATENT DOCUMENTS

| | | | |
|---|---|---|---|
| 5,269,314 A | 12/1993 | Kendall et al. | |
| 5,466,898 A * | 11/1995 | Gilbert | A61B 7/02 181/131 |
| 5,486,659 A * | 1/1996 | Rosenbush | A61B 7/02 181/131 |
| 5,564,431 A | 10/1996 | Seward | |
| 5,623,131 A * | 4/1997 | Earnest | A61B 7/02 128/DIG. 15 |
| 5,747,751 A * | 5/1998 | Weckerle | A61B 7/02 181/131 |
| 6,006,856 A * | 12/1999 | Skubal | A61B 7/02 181/131 |
| 6,467,568 B1 | 10/2002 | Kemper | |
| 6,575,917 B2 * | 6/2003 | Giroux | A61B 7/02 181/131 |
| 7,575,094 B1 * | 8/2009 | Rosenberg | A45C 13/002 181/131 |
| 7,614,477 B2 * | 11/2009 | Statner | A61B 46/10 181/131 |
| 7,823,690 B2 | 11/2010 | Hirsch et al. | |
| 2002/0170771 A1 * | 11/2002 | Milam | B62D 5/0406 180/443 |
| 2007/0193822 A1 * | 8/2007 | Statner | A61B 46/10 181/131 |

(Continued)

*Primary Examiner* — Forrest M Phillips
(74) *Attorney, Agent, or Firm* — Global Intellectual Property Agency, LLC; Daniel Boudwin

(57) ABSTRACT

A stethoscope protective cover for shielding a stethoscope head. The stethoscope protective cover is a sleeve with an open end and a closed end configured to fit closely around the diaphragm or bell of a stethoscope chest piece. The sleeve is made from an acoustically transmissive material, ensuring that the acoustical vibrations from a patient's body are minimally affected when the sleeve covers the chest piece. A first fastener and second fastener are placed toward the open end of the sleeve, with a slot between them that allows for the tubing of a stethoscope to extend therethrough. A tab is placed near the open end of the stethoscope protective cover to facilitate opening the sleeve and placing the stethoscope chest piece therein.

12 Claims, 3 Drawing Sheets

(56) References Cited

U.S. PATENT DOCUMENTS

2009/0020357 A1* 1/2009 Pack-Walden ....... B65D 33/002
 181/131
2009/0288908 A1* 11/2009 Giroux ..................... A61B 7/02
 181/131

* cited by examiner

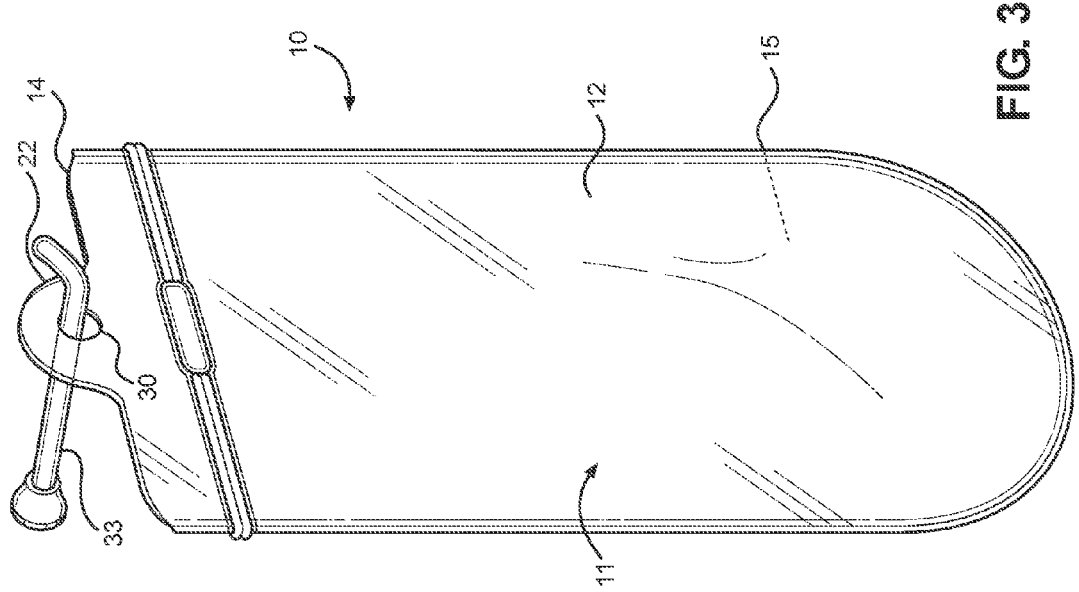

STETHOSCOPE PROTECTIVE COVER

CROSS REFERENCE TO RELATED APPLICATIONS

This application claims the benefit of U.S. Provisional Application No. 62/236,380 filed on Oct. 2, 2015. The above identified patent application is herein incorporated by reference in its entirety to provide continuity of disclosure.

BACKGROUND OF THE INVENTION

The present invention relates to stethoscope covers. More specifically, the present invention relates to stethoscope covers that offers protection of the chest piece of a stethoscope without impeding its functionality.

The chest piece of a stethoscope can be one of the most contaminated surfaces in a hospital. Listening to the heart beat or the breathing of a patient is a vital and common assessment tool for a health care provider. As a result, a stethoscope head used in a health care setting often comes into constant contact with many patients having a variety of medical maladies. Dangerous infections such as MRSA, VRE, CRE, C. Diff, hepatitis, along with other contagious diseases, are responsible for many extended hospitalization stays, chronic illnesses, and deaths every year. These infections can easily spread from one patient to another, or from a patient to a health care provider, if a stethoscope is not properly protected.

While stethoscope covers exists in the prior art, many are cumbersome to use. Specifically, it can be difficult to maneuver a stethoscope into an appropriate cover. Even slight inconveniences can dissuade a doctor from using such a cover, especially when circumstances provide for limited time. Accordingly, a cover that can be easily opened and used with minimal effort is desired.

SUMMARY OF THE INVENTION

In view of the foregoing disadvantages inherent in the known types of stethoscope covers now present in the prior art, the present invention provides a stethoscope cover wherein the same can be utilized for providing convenience for the user when wishing to protect a stethoscope chest piece. The present system comprises a sleeve having an open end and a closed end, wherein the closed end is configured to fit around the diaphragm or bell of a stethoscope chest piece to a close tolerance. The sleeve comprises an acoustically transmissive material, ensuring that the acoustical vibrations from a patient's body are minimally affected. A first fastener and second fastener are disposed toward the open end of the sleeve, with a slot placed therebetween to allow for the tubing of a stethoscope to extend therethrough. A tab is placed near the open end to facilitate opening the sleeve and placing the stethoscope chest piece therein.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

FIG. 3 shows a perspective view of the stethoscope protective cover with an aperture for hanging the stethoscope protective cover from a hanging peg.

DETAILED DESCRIPTION OF THE INVENTION

Figure 1:
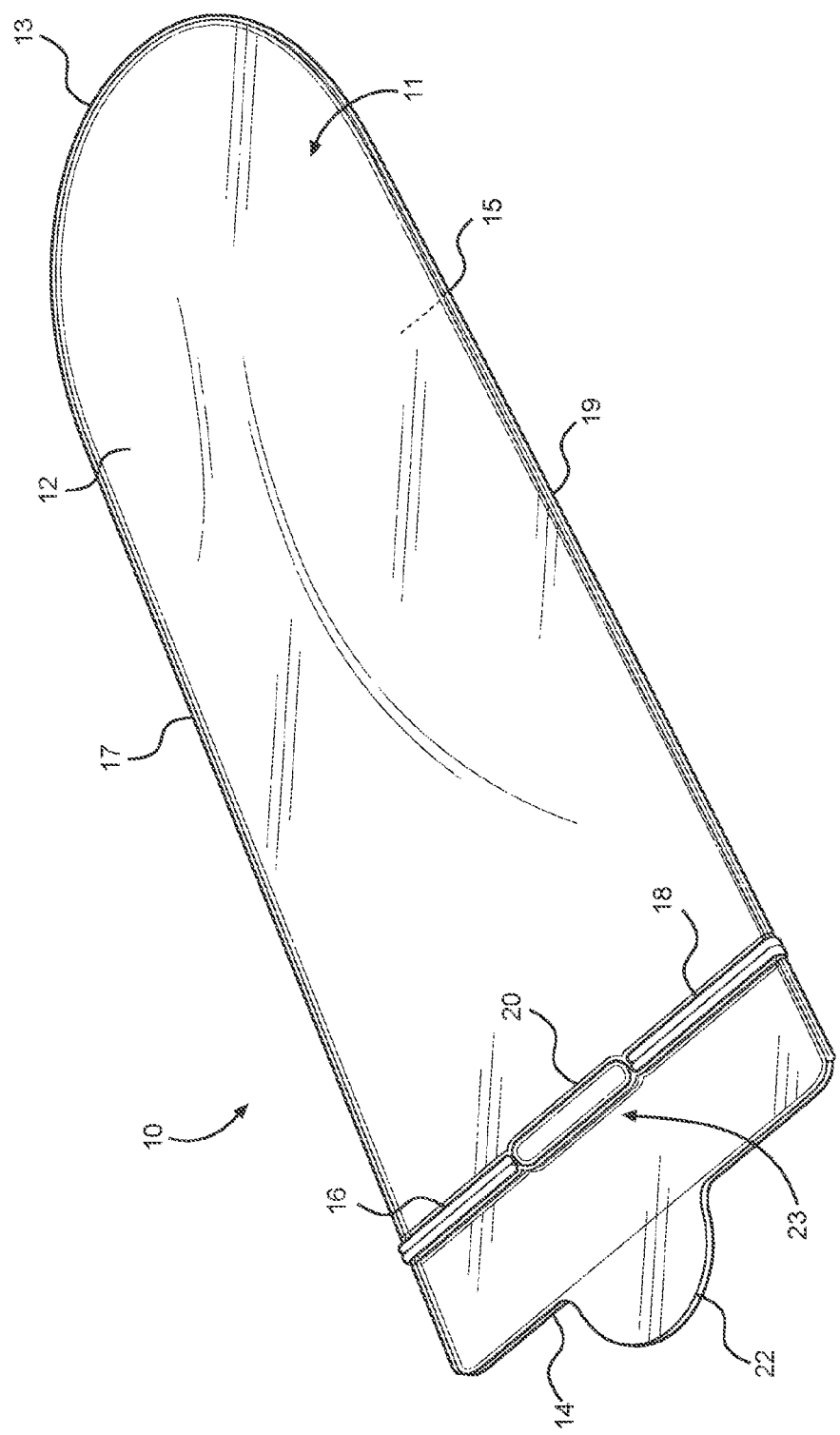
FIG. 1 shows a perspective view of one embodiment of the stethoscope protective cover.

Reference is made herein to the attached drawings. Like reference numerals are used throughout the drawings to depict like or similar elements of the stethoscope protective cover. The figures are intended for representative purposes only and should not be considered to be limiting in any respect.

Referring now to FIG. 1, there is shown a perspective view of the stethoscope protective cover. The stethoscope protective cover 10 comprises an enclosed sleeve 11 having a proximal end 14 with an opening and a distal end 13 forming a closed edge. The sleeve 11 further comprises a first fastener 16 and a second fastener 18, configured to seal the proximal end 14 closed. A tab 22 extends outward from the proximal end 14 of the sleeve 11. In some embodiments of the stethoscope protective cover 10, a tab 22 is disposed on a front wall 12 of the sleeve 11 and a corresponding secondary tab is disposed on a rear wall 15 of the sleeve 11.

The first fastener 16 is positioned toward the proximal end 14 and extends perpendicular from a first side edge 17 of the sleeve 11 toward a mid-section 23. Likewise, the second fastener 18 is positioned toward the proximal end 14 and extends perpendicular from a second side edge 19 of the sleeve 11 toward the mid-section 23. In some embodiments of the stethoscope protective cover 10, the first fastener 16 and second fastener 17 comprise interlocking rib and groove elements. For example, the rib element may be disposed on the front wall 12 and the groove element may be disposed on the rear wall 15. When pressed together, the interlocking elements create a seal. Further embodiments of the stethoscope protective cover 10 use alternative fasteners, such as hook and loop material.

The mid-section 23 is disposed an equal distance between the first edge 17 and second edge 19 of the sleeve 11. When the opening of the proximal end 14 has been secured via the first fastener 16 and second fastener 18, an unsealed slot 20 remains positioned in the mid-section between the two fasteners 16, 18, where the front wall 12 and rear wall 15 remain unconnected. The slot 20 has a width sufficient to allow the tubing of a stethoscope to fit therein. The unsealed slot 20 can further include a coating of a tacky substance along an interior surface thereof. The tacky coating on the unsealed slot 20 assists in securing the tubing of a stethoscope in order to prevent the cover 11 from sliding distally along the stethoscope tubing.

Figure 2:
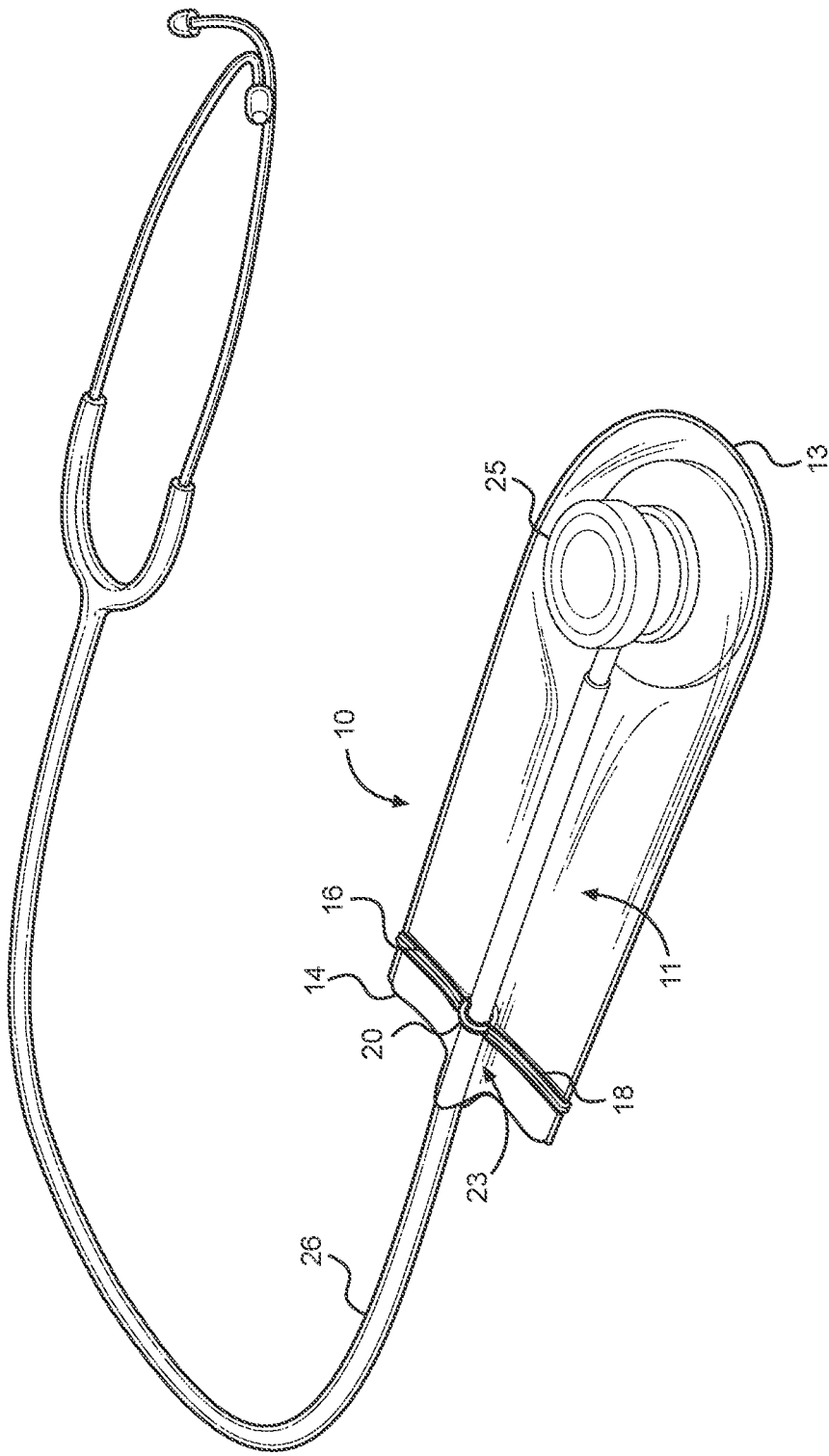
FIG. 2 shows a perspective view of one embodiment of the stethoscope protective cover placed over the chest piece end of a stethoscope.

Referring now to FIG. 2, there is shown a perspective view of the stethoscope protective cover placed on the distal end of a stethoscope. In use, the sleeve 11 is opened at the proximal end 14 and the chest piece 25 of a stethoscope is placed within the interior of the sleeve 11 of the stethoscope protective cover 10. The first fastener 16 and the second fastener 18 are secured closed, and the tubing 26 of the stethoscope extends through the unsealed slot 20. The sleeve 11 further comprises an acoustically transmissive material, such that when the chest piece 25 of the stethoscope is placed against the body of a patient, acoustic vibrations are able to pass through the sleeve 11 to the bell or the diaphragm of the chest piece 25 with minimal vibrational loss, allowing a medical professional to use the stethoscope protective cover without any hindrance to the functionality of the stethoscope. Examples of acoustically transmissive materials include polyethylene or similar plastics. In some embodiments of the stethoscope protective cover, the sleeve 11 further comprises a transparent material, allowing for visual inspection of the stethoscope head 25 without removing it from the interior of the sleeve 11. The ability to visually inspect the stethoscope head 25 allows the user to see whether the bell or the diaphragm of the head 25 is in position for use, which in turn allows the user to rotate the head 25 to either the bell or the diaphragm, without removing it from the interior of the sleeve 11. The distal end 13 is configured to fit around the chest piece 25 to a close tolerance, minimizing bulky excess that may interfere with the stethoscope use. In some embodiments of the stethoscope protective cover 10, the distal end 13 is configured in a semicircular shape to conform more closely to the circumference of the chest piece 25.

Referring now to FIG. 3, there is shown a perspective view of the stethoscope protective cover with an aperture for hanging the stethoscope protective cover from a hanging peg. In some embodiments of the stethoscope protective cover 10, there is an aperture 30 disposed on the tab 22 extending from the distal end 14 of the stethoscope protective cover 10. In embodiments having a tab 22 on both the front wall 12 and rear wall 15, there is an aperture 30 disposed on both tabs 22 and aligned to overlap with each other, allowing a hanging peg 33 to extend through both apertures. In other embodiments, the stethoscope protective cover 10 lacks an aperture 30 for storing the covers 10 by hanging them from a peg 33. In this embodiment, the cover 10 is instead provided in a dispenser, e.g., a spring-loaded dispenser that stores the covers 10 and allows them to be removed individually as needed.

The tab 22 disposed on the front wall 12 of the stethoscope protective cover 10 is adapted to be grasped, allowing a user to pull on it and open the proximal end 14 of the sleeve 11. This allows the stethoscope head to be lowered into the interior while it is still secured to the hanging peg 33, decreasing the possibility of germs or unwanted matter entering the interior and contaminating the stethoscope head. The stethoscope protective cover 10 can then be removed from the hanging peg 33. This configuration allows for convenient single handed use. In some embodiments of the stethoscope protective cover 10, multiple sleeves are provided in a stack and held together by a low force fastener, such as small perforated tabs, providing for easy handing of many sleeves, such as when mounting on a hanging peg, while allowing a single sleeve to be easily separated from the stack.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A stethoscope protective cover, comprising:
an acoustically transmissive sleeve having an open proximal end, a closed distal end, a first side edge and a second side edge, defining an interior volume;
a first fastener disposed toward the proximal end, extending perpendicularly from the first side edge toward a mid-section;
a second fastener disposed toward the proximal end, extending perpendicularly from the second side edge toward the mid-section;
wherein the first fastener terminates at a first lateral side of the slot and the second fastener terminates at an opposing second lateral side of the slot forming an unclosable slot via the first and second fasteners;
wherein a slot is disposed between the first fastener and second fastener, the slot adapted to form a seal around a tubing of a stethoscope to fit therein;
a tab disposed on the proximal end and extending therefrom wherein the tab is configured to assist in unsecuring each of the first fastener and the second fastener.

2. The stethoscope protective cover of claim 1, wherein the sleeve comprises a front wall and a rear wall.

3. The stethoscope protective cover of claim 2, wherein the tab is disposed on the front wall and a secondary tab is disposed on the rear wall and configured to unsecure each of the first fastener and the second fastener when the tab on the front wall is separated from the tab on the second wall.

4. The stethoscope protective cover of claim 1 wherein the tab is centrally positioned between the first edge and the second edge.

5. The stethoscope protective cover of claim 1, the tab further comprising an aperture adapted to have a support member inserted-therethrough.

6. The stethoscope protective cover of claim 3, the tab and secondary tab further comprising corresponding apertures-adapted to have a support member inserted-therethrough.

7. The stethoscope protective cover of claim 1, wherein the distal end further comprises a semi-circular shape adapted to fit a stethoscope chest piece to a close tolerance.

8. The stethoscope protective cover of claim 1, wherein the first fastener comprises a rib element and the second fastener comprises a groove element, wherein the rib element is adapted to interlock within the groove element.

9. The stethoscope protective cover of claim 1, wherein a tacky material is disposed along an interior surface of the slot.

10. The stethoscope protective cover of claim 1, wherein at least a segment of the acoustically transmissive sleeve is transparent.

11. The stethoscope protective cover of claim 1, wherein the first fastener and the second fastener are disposed between the proximal end and the distal end.

12. The stethoscope protective cover of claim 1, wherein each of the first fastener and the second fastener extends to and contacts each of the first side edge and the second side edge of the acoustically transmissive sleeve respectively.

* * * * *